US010987055B2

(12) United States Patent
Gerlitz

(10) Patent No.: US 10,987,055 B2
(45) Date of Patent: Apr. 27, 2021

(54) SUBSTANCE CONCENTRATION NIR MONITORING APPARATUSES AND METHODS

(71) Applicant: GlucoVista Inc., Fairfield, NJ (US)

(72) Inventor: Yonatan Gerlitz, Herzliya (IL)

(73) Assignee: GlucoVista Inc., Fairfield, NJ (US)

(*) Notice: Subject to any disclaimer, the term of this patent is extended or adjusted under 35 U.S.C. 154(b) by 332 days.

(21) Appl. No.: 15/985,015

(22) Filed: May 21, 2018

(65) Prior Publication Data
US 2018/0333100 A1 Nov. 22, 2018

Related U.S. Application Data

(60) Provisional application No. 62/508,880, filed on May 19, 2017.

(51) Int. Cl.
*A61B 5/00* (2006.01)
*G01K 13/00* (2021.01)
(Continued)

(52) U.S. Cl.
CPC .............. *A61B 5/6816* (2013.01); *A61B 5/01* (2013.01); *A61B 5/1455* (2013.01);
(Continued)

(58) Field of Classification Search
CPC ....... A61B 5/6816; A61B 5/7289; A61B 5/01; A61B 5/1455; A61B 5/14532; G01K 13/002; G01N 21/359; G01N 33/49
See application file for complete search history.

(56) References Cited

U.S. PATENT DOCUMENTS 5,676,143 A 10/1997 Naganuma et al.
5,737,078 A 4/1998 Takarada et al.
(Continued)

FOREIGN PATENT DOCUMENTS

EP 0074428 4/1987
WO 9115990 10/1991
(Continued)

OTHER PUBLICATIONS

Notification of Transmittalof The International Search Reort and The Written Opinion of The International Searching Authority, or The Declaration, PCT/US2018/033695, dated Sep. 3, 2018.
(Continued)

*Primary Examiner* — Eric F Winakur
*Assistant Examiner* — Abid A Mustansir
(74) *Attorney, Agent, or Firm* — Randall Danskin, P.S.

(57) ABSTRACT

A substance concentration monitoring method includes inserting a temperature probe noninvasively into a volume of a body in which a concentration of a substance is to be measured. An internal temperature of the volume is measured and an internal temperature signal is produced. An incident first near infrared beam in a first wavelength band is directed from a light source into a portion of the volume, the first wavelength band including a wavelength at which an absorption peak exists in a NIR absorption spectrum of the substance. An incident second NIR beam in a second wavelength band is directed from the light source into the portion of the volume, the substance exhibiting no absorption or negligible absorption in the second wavelength band. Substance concentration is calculated based on values corresponding to the internal temperature signal, a first and second initial power signal, and a first and second material absorption signal.

19 Claims, 1 Drawing Sheet

(51) Int. Cl.
*G01N 21/359* (2014.01)
*A61B 5/01* (2006.01)
*A61B 5/1455* (2006.01)
*A61B 5/145* (2006.01)
*G01N 33/49* (2006.01)

(52) U.S. Cl.
CPC ........ *A61B 5/14532* (2013.01); *A61B 5/7289* (2013.01); *G01K 13/002* (2013.01); *G01N 21/359* (2013.01); *G01N 33/49* (2013.01)

(56) References Cited

U.S. PATENT DOCUMENTS

| | | | |
|---|---|---|---|
| 8,401,604 | B2 | 3/2013 | Gerlitz |
| 8,611,975 | B2 | 12/2013 | Gerlitz |
| 9,795,329 | B2 | 10/2017 | Gerlitz |
| 2007/0197886 | A1 | 8/2007 | Simonsen et al. |
| 2007/0201028 | A1 | 8/2007 | Myers et al. |
| 2007/0203405 | A1 | 8/2007 | Shimomura |
| 2010/0030041 | A1* | 2/2010 | Bruinsma ............ A61B 5/6826 600/322 |
| 2011/0004080 | A1 | 1/2011 | Gerlitz et al. |
| 2011/0245713 | A1* | 10/2011 | Rensen .................... G01K 3/14 600/549 |
| 2015/0196233 | A1* | 7/2015 | Gerlitz ................. A61B 5/0059 600/301 |
| 2015/0366490 | A1* | 12/2015 | Gerlitz ................... A61B 5/747 600/316 |
| 2017/0311854 | A1 | 11/2017 | Gerlitz et al. |

FOREIGN PATENT DOCUMENTS

| | | |
|---|---|---|
| WO | WO2010033104 | 3/2010 |
| WO | 2015164845 | 10/2015 |

OTHER PUBLICATIONS

International Searching Authority, International Search Report and Written Opinion for Application No. PCT/US2015/011062 dated Apr. 2, 2015, dated Apr. 2, 2015.

* cited by examiner

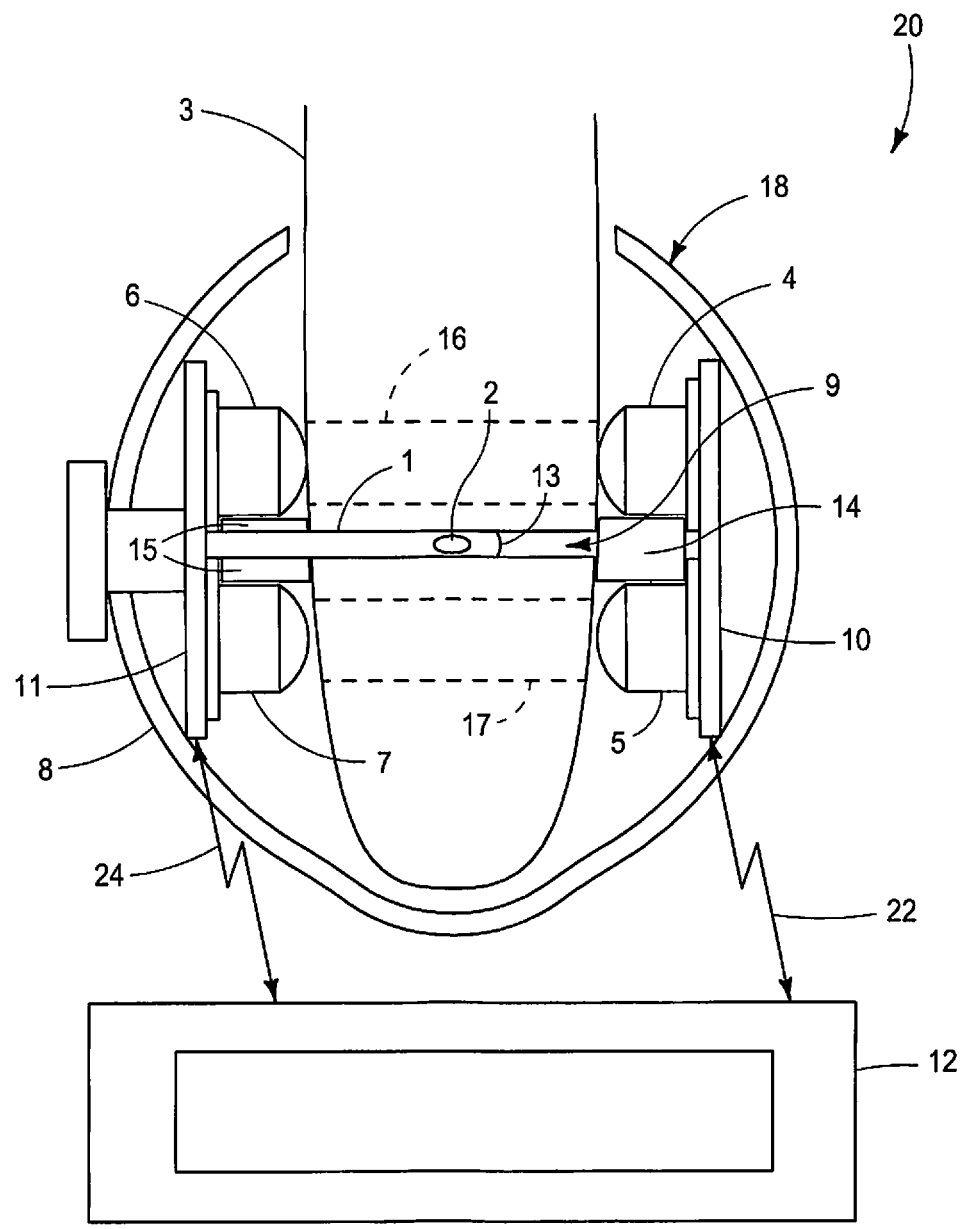

SUBSTANCE CONCENTRATION NIR MONITORING APPARATUSES AND METHODS

CROSS REFERENCE TO RELATED APPLICATIONS

This application claims the benefit of priority under 35 U.S.C. § 119 to U.S. Provisional Patent Application No. 62/508,880, filed on May 19, 2017 and entitled "Non-Invasive Apparatus for Continuous Measurement of Body Ingredients In-Vivo, Using Near Infrared Spectroscopy," which is hereby incorporated by reference in its entirety.

BACKGROUND

Determining an amount or a concentration of glucose within a body may be valuable for many purposes. Some benefits of determining a concentration of glucose within a body include health benefits, such as diagnosing and treating health issues, research benefits, health monitoring benefits, and many more benefits. Unfortunately, determining a concentration of glucose in a body may include invasive testing that may be painful or harmful to a subject.

Systems for non-invasively measuring a concentration of glucose are under development. Such systems often rely on a correlation between an amount of light absorbed through the body and the concentration of glucose. However many factors and lurking variables may affect the amount of light absorbed. Known systems for non-invasively measuring a concentration of glucose in a body may be less accurate because they do not take into account parameters in addition to the amount of light absorbed through the body that may also correlate to the concentration of glucose. Accordingly, systems and methods capable of greater accuracy would be beneficial.

SUMMARY

A substance concentration monitoring method includes inserting a temperature probe noninvasively into a volume of a body in which a concentration of a substance is to be measured, the temperature probe contacting an internal surface of the volume. An internal temperature of the volume is measured as determined by heat transfer from the internal surface to the inserted temperature probe and an internal temperature signal is produced indicative of the internal temperature.

While the volume exhibits the internal temperature, an incident first near infrared (NIR) beam in a first wavelength band is directed from a light source into a portion of the volume, the first wavelength band including a wavelength at which an absorption peak exists in a NIR absorption spectrum of the substance. While directing the incident first NIR beam, an initial power of the incident first NIR beam is detected and a first initial power signal indicative of the first initial power is produced. While the volume exhibits the internal temperature, the first NIR beam exiting from the portion of the volume is received onto a detector. While receiving the exiting first NIR beam, an exit power of the exiting first NIR beam not absorbed in the volume is detected and a first material absorption signal indicative of the first exit power is produced.

Additionally, while the volume exhibits the internal temperature, an incident second NIR beam in a second wavelength band is directed from the light source into the portion of the volume, the substance exhibiting no absorption or negligible absorption in the second wavelength band. While directing the incident second NIR beam, an initial power of the incident second NIR beam is detected and a second initial power signal indicative of the second initial power is produced. While the volume exhibits the internal temperature, a second NIR beam exiting from the portion of the volume is received onto the detector. While receiving the exiting second NIR beam, an exit power of the exiting second NIR beam not absorbed in the volume is detected and a second material absorption signal indicative of the second exit power is produced.

The method includes calculating substance concentration in the portion of the volume based on values corresponding to the internal temperature signal, the first and second initial power signal, and the first and second material absorption signal.

A substance concentration monitoring apparatus includes a casing, a slot in the casing sized and positioned to receive an ear lobe, and a temperature probe inside the casing sized and positioned to extend into the slot and to be received into a healed piercing of the ear lobe when the ear lobe is placed in the slot. The temperature probe includes a thermally conductive needle with a thermistor inside the needle or with a resistance temperature detector.

A light source is inside the casing and is configured to produce a first near infrared (NIR) beam in a first wavelength band and to produce a second NIR beam in a second wavelength band. The light source is positioned and oriented to direct the first and second NIR beams through the ear lobe when the ear lobe is placed in the slot. The first wavelength band includes a wavelength at which an absorption peak exists in a NIR absorption spectrum of the substance. The substance exhibits no absorption or negligible absorption in the second wavelength band.

A NIR detector is inside the casing on an opposing side of the slot from the light source and is positioned to be on an opposing side of the ear lobe from the light source when the ear lobe is placed in the slot. The detector is aligned with the light source to receive the first and second NIR beams from the light source directed through and exiting from the ear lobe when the temperature probe is inserted into the piercing. The NIR detector is configured to detect an exit power of the first NIR beam and the second NIR beam.

The temperature probe is positioned in proximity to the light source and the detector such that a temperature of the ear lobe measured by the temperature probe corresponds to an internal temperature of a volume of the ear lobe through which the first and second NIR beams are directed when the temperature probe is inserted into the piercing.

The features, functions, and advantages that have been discussed can be achieved independently in various embodiments or may be combined in yet other embodiments further details of which can be seen with reference to the following description and drawings.

BRIEF DESCRIPTION OF THE DRAWINGS

Some embodiments are described below with reference to the following accompanying drawing.

The drawing is a schematic illustration of the general construction of a device for non-invasively measuring substance concentration in the body.

DETAILED DESCRIPTION

Disclosed herein are methods and apparatuses to non-invasively monitor a concentration of a substance of interest within a body. The monitoring may occur continuously. As an example, the embodiments described herein may be used to continuously monitor a concentration of glucose in a person's blood. Some of the embodiments described herein may be worn for periods of time that range from several minutes to days.

In the context of the present document, "continuous" monitoring refers to measuring substance concentration over time while the monitoring apparatus continues to contact the body between consecutive measurements. That is, even though the monitoring apparatus may be programmed to take a measurement at periodic intervals, any interval may be selected. The monitoring apparatus is capable of taking a measurement at any time since it is not removed from contact with the body between consecutive measurements. An operator may program a selected measurement interval. Also, the monitoring apparatus may automatically change measurement intervals, depending on programmed conditions. For example, more frequent measurement may be warranted when concentration approaches a level of concern.

As the apparatus is worn on a body, the concentration of the substance within the body may be continuously monitored by determining whether substance concentrations or a consecutive plurality of data sets indicative of the concentration of the substance are within a tolerance. For example, as new data sets are generated at a processor, the new data sets may be compared to one or more tolerances. Alternatively or additionally, the concentrations may be compared to one or more tolerances. The tolerances may be stored in the memory of the apparatus. If the new data set or concentration is outside the tolerance, such as less than a lower tolerance or greater than an upper tolerance, a warning output may be generated and sent to the display device. Alternatively or in addition, the warning output may be sent to a wireless transmitter.

The wireless transmitter may be configured to send the warning output to a remote device. The remote device may include a cellular telephone, a tablet, a laptop, or another type of mobile computing device. The warning output may indicate to the remote device to display a warning. The warning output may further indicate to the mobile device to contact an emergency service.

Most of the organic molecules in the body have specific absorption and emission spectra in the near infrared (NIR). Those spectra may be used to make quantitative analysis of the concentration of the molecules in the body. The main draw-back of measurement in the near infrared is the strong dependence of the absorption/emission spectrum on the temperature of the molecules.

The light sources of the apparatuses and methods herein may include an infrared (IR), such as a near-infrared (NIR), emitter to generate IR light, such as NIR light in the range of 750 nm to 6,000 nanometers (nm). Further, in some apparatuses and methods, the light source may be configured to selectively generate light in a first wavelength band and a second wavelength band. The first wavelength band may include wavelengths, particularly in the IR region or NIR region, where a substance, such as glucose, has an effect on absorption of transmitted light.

For example, the first wavelength band may be within the range of about 1130 nm to about 1190 nm (e.g., a 1160 nm operating wavelength) or within the range of 1300 nm to 1500 nm (e.g., a 1460 nm operating wavelength). The second wavelength band may include wavelengths where the substance has no effect or negligible effect on absorption of transmitted light. For example, the second wavelength band may be within the range of about 800 nm to about 905 nm (e.g., a 870 nm or a 880 nm operating wavelength), or may be within a range that includes a 960 nm or a 1120 nm operating wavelength. Beneficially, the first wavelength may be 1160 nm and the second wavelength may be 960 nm. Some apparatuses and methods may include two light sources, as described below.

For example to measure glucose concentration with accuracy of 5 milligrams (mg)/per deciliter (dL) the temperature should be measured with an accuracy of 0.01 K (Kelvin) or less than 0.01 K. Thus, a method of accurately measuring temperature inside the part of the body where infrared measurement is being performed may enable quantitative analysis of ingredients in the body (in vivo).

The target of one apparatus and method is to enable measurement of a quantitative infrared spectrum of body composition by accurate measurement of the temperature inside the body in the area/volume where NIR measurement is performed.

One possible apparatus, having a shape of an earring, is placed on the earlobe where the piercing needle acts as a temperature probe with a tube containing inside an accurate thermistor. The tube may be made with gold or aluminum coated with gold for high thermal conductivity. The gold or aluminum coated with gold is also biocompatible. Known temperature probes for surgical procedures exist using similar materials. Here, the temperature probe is placed in a healed piercing, that is, a passage through body tissue lined with skin cells. Such a passage is a type of fistula and could conceivably be formed in other parts of the body compatible with the methods and apparatuses herein. The thermistor measures the temperature inside the earlobe; thermally isolating material is applied around the needle on both sides of the earlobe.

The thermal isolation creates a temperature cavity across the earlobe to increase uniformity of the temperature through the optical path and to avoid temperature changes due to changes in ambient temperature. Due to the high thermal conductivity of the needle and the thermal isolation, the thermistor measures the average temperature of the optical path through the body.

The internal temperature of the volume being measured in the methods and apparatuses herein may be determined at least by conductive heat transfer from an internal surface of the volume to the inserted temperature probe. Depending on a size of a passage compared to a size of the temperature probe, which determines contact area, heat transfer may additionally include radiative and/or convective heat transfer. However, conductive heat transfer allows the fastest heat transfer. Accordingly, a temperature probe may be sized to increase contact area with an intended passage to provide higher thermal contact.

The material of the piercing needle may be used as a resistance temperature detector (RTD) instead of providing a thermistor inside the needle. If the needle itself is a RTD, then the tube may be made with nickel or platinum. Otherwise, many RTD elements include of a length of fine wire wrapped around a ceramic or glass core. The RTD wire is a pure material, often platinum, nickel, or copper. The material has an accurate resistance/temperature relationship which is used to provide an indication of temperature. As other RTD elements are often fragile, they may be housed in protective probes.

Two near infrared emitters, or one near infrared emitter with changeable wavelength, are placed in the earring on one side of the earlobe so the path of the beam (optical path) is as close as possible to the piercing needle. Keeping the emitters as close as possible permits the measured temperature to accurately represent the temperature along the beam path. The actual distance from the temperature probe within which measured temperature will accurately reflect actual temperature along the beam path may vary based on temperature gradients in tissue, which are governed by body temperature, ambient temperature, and body composition. On the other side of the earlobe, one or two detectors with a matching bandwidth filter(s) are positioned to measure the absorbance through the earlobe. The emitting device includes a detection means for measuring the initial power of the infrared beam (10). The detection means may be a detector with a photodiode and may be installed in a feedback loop that controls the beam power from the emitting device. A first infrared beam should be in a wavelength band where the material has no absorption or negligible absorption, while the second infrared beam should be in a wavelength band where the material for quantitative analyzing has a peak absorption in its spectrum.

A first filter may include an interference filter configured to pass light within a first wavelength band. The first wavelength band may correspond to a wavelength band of light emitted by a first light source and may include wavelengths in which a substance affects absorption of light by the body. Further, the first filter may block light within a second wavelength band, where the substance has no or negligible effect on absorption of light by the body. By blocking light within the second wavelength, the first filter may reduce interference at the detector from light within the second wavelength band. Further, the first filter may block ambient light, thereby also reducing interference from ambient light at the detector. The function of the first filter may be accomplished by multiple filters.

A second filter may also include an interference filter. For example, the second filter may be configured to block light within the first wavelength band, corresponding to a wavelength band in which the substance affects absorption of light by the body. Further, the second filter may pass light within the second wavelength band, where the substance has no or negligible effect on absorption of light by the body. By blocking light within the first wavelength, the second filter may reduce interference at the detector from light within the first wavelength band. The second filter may further block ambient light, thereby also reducing interference from ambient light at the detector. The function of the second filter 282 may be accomplished by multiple filters.

Although two filters are possible, some methods and apparatuses may use a single filter. In such case, the first wavelength band may include a wavelength band where glucose affects absorption of light and the second wavelength band may be an entire NIR spectrum emitted by the light source 210. Measurements within the first wavelength band may be performed using the single filter and measurements within the second wavelength band may be performed while the single filter 280 is not present. Further, in some methods and apparatuses, both the first filter and the second filter may be omitted. In such case, the light sources may use single wavelength emitters to apply only those wavelengths that fall within the first wavelength band for one light source and within the second wavelength band for another light source. As described herein, a single light source may selectively apply wavelengths that fall within the first wavelength band and wavelengths that fall within the second wavelength band.

Signals from the thermistor and signals from the detector(s) may be transferred through an analog to digital conversion device to a microprocessor to be analyzed and stored.

An example of a method of calibrating the device is a personal calibration, creating a look-up table of measured signals (material absorption and IO signals, reference absorption and IO signals, and temperature signal) correlated to in-vivo gold standard measurement of the ingredients in the blood. This look-up table continuously translates the results of the measurements to the ingredient's concentration in the blood through the correlation and this concentration is shown on a display device for the user. As an alternative to a look-up table, a function or formula may be derived that relates the measurements to the ingredient's concentration in the blood. Examples of implementing look-up tables and functions or formulas for correlation to concentration will be appreciated from U.S. Pat. No. 8,401,604 to Gerlitz issued Mar. 19, 2013, U.S. Pat. No. 8,611,975 to Gerlitz issued Dec. 17, 2013, U.S. patent application Ser. No. 12/883,063 by Gerlitz filed Sep. 15, 2010, U.S. patent application Ser. No. 14/745,180 by Gerlitz filed Jun. 19, 2015, and U.S. patent application Ser. No. 15/653,428 by Gerlitz filed Jul. 18, 2017.

The measurement result can be further transferred to a smartphone device where it may be stored, displayed as a graph, and/or used for calculation of other quantitative parameters useful for medical treatment. The smartphone may also be used to send an alert to the user or to an appointed physician, in case of dangerous concentration levels of the ingredients.

The paragraphs following below include a brief description of the drawing.

Measurement system 20 includes earring assembly 18 and control box 12. Needle 1 is inserted in earlobe 3 and extends partly through tube 9, which is a healed piercing. Thermistor 2 inside needle 1 may be removed with needle 1 instead operating as a resistance temperature detector (RTD). Earlobe 3 may be pierced in advance. Tube 9 is shown as a piercing of the ear lobe healed to form a fistula, meaning a passage through body tissue lined with skin cells. Tube 9 is distinguished from incisions and punctures since needle 1 placed in tube 9 does not contact body fluids. Tube 9 could conceivably be provided in other body tissues capable of accommodating a light source, such as light sources 4, 5, and an opposing detector assembly, such as detector assembly 6, 7.

Light sources 4, 5 are shown as separate NIR emitters, but may be a single NIR emitter. Although light sources capable of selectively generating multiple wavelengths are known, the greatest flexibility in choosing desired and less costly light sources for generating light in the wavelengths of interest involves using multiple emitters. A single emitter allows size reduction of earring assembly 18. Detector assemblies 6, 7 have matching bandpass filters corresponding to the opposing light source. Light sources 4, 5 are shown with lenses mounted thereon for directing beams into earlobe 3. Detector assemblies 6, 7 are shown with lenses mounted thereon for receiving beams and directing beams onto a detector (not shown). Optical paths 16, 17 through earlobe 3 coincide with the paths of beams from light sources 4, 5 to detector assemblies 6, 7.

Casing 8 contains light sources 4, 5, light chassis 10, detector assemblies 6, 7, detector chassis 11, needle 1, thermistor 2, and thermal isolation 14, 15. Additional thermal isolation material aside from that immediately around needle 1 is not shown in the drawing for simplicity. Even so, casing 8 could itself provide thermal isolation from ambient temperature changes when formed from a thermally isolating material, such as an insulating polymer. Light chassis 10 includes a small printed circuit board assembly (PCBA)

including pre-amplifiers, an analog-to-digital (ATD) converter(s), and a transmitter-receiver. Detector chassis 11 includes a small PCBA including pre-amplifiers, an ATD(s), and a transmitter-receiver.

Control box 12 includes a transmitter-receiver device (not shown), a microprocessor (not shown), a display (not shown), and a user interface (not shown). The microprocessor may perform the processor functions described elsewhere herein. The microprocessor may include integrated memory and/or additional memory may be provided for storing data sets, a look-up table, calibration data, concentration correlation data, etc. The transmitter-receiver device may be one device or multiple devices configured for wireless, two-way communication 22 with light chassis 10 and wireless, two-way communication 24 with detector chassis 11. The FIGURE shows wireless communications 22, 24, but wired communication could conceivably be used, though it might suffer from the disadvantage of adding bulk to measurement system 20. Control box 12 could be a dedicated apparatus with no functions other than those pertaining to measurement system 20, or the functions of control box 12 might be provided by a general purpose computer, such as a smart phone.

According to one method, monitoring substance concentration includes inserting a temperature probe noninvasively into a volume of a body in which a concentration of a substance is to be measured, the temperature probe contacting an internal surface of the volume. An internal temperature of the volume is measured as determined by heat transfer from the internal surface to the inserted temperature probe and an internal temperature signal is produced indicative of the internal temperature.

While the volume exhibits the internal temperature, an incident first near infrared (NIR) beam in a first wavelength band is directed from a light source into a portion of the volume, the first wavelength band including a wavelength at which an absorption peak exists in a NIR absorption spectrum of the substance. While directing the incident first NIR beam, an initial power of the incident first NIR beam is detected and a first initial power signal indicative of the first initial power is produced. While the volume exhibits the internal temperature, the first NIR beam exiting from the portion of the volume is received onto a detector. While receiving the exiting first NIR beam, an exit power of the exiting first NIR beam not absorbed in the volume is detected and a first material absorption signal indicative of the first exit power is produced.

Additionally, while the volume exhibits the internal temperature, an incident second NIR beam in a second wavelength band is directed from the light source into the portion of the volume, the substance exhibiting no absorption or negligible absorption in the second wavelength band. While directing the incident second NIR beam, an initial power of the incident second NIR beam is detected and a second initial power signal indicative of the second initial power is produced. While the volume exhibits the internal temperature, a second NIR beam exiting from the portion of the volume is received onto the detector. While receiving the exiting second NIR beam, an exit power of the exiting second NIR beam not absorbed in the volume is detected and a second material absorption signal indicative of the second exit power is produced.

The method includes calculating substance concentration in the portion of the volume based on values corresponding to the internal temperature signal, the first and second initial power signal, and the first and second material absorption signal.

Additional features may be implemented in the present method. By way of example, the substance may be glucose. Inserting the temperature probe noninvasively may include inserting the temperature probe into a healed piercing of an ear lobe with the light source and the detector positioned on opposing sides of the ear lobe. The light source may be a single NIR emitter configured to generate selectively a NIR beam in the first wavelength band and to generate selectively a NIR beam in the second wavelength band. Correspondingly, the detector may be a single detector configured to detect the NIR beams both in the first wavelength band and in the second wavelength band. Alternatively, the light source may be a first NIR emitter configured to generate a first NIR beam in the first wavelength band and a different second NIR emitter configured to generate a second NIR beam in the second wavelength band. Correspondingly, the detector may be a first detector configured to detect the NIR beam in the first wavelength band and a different second detector configured to detect the NIR beam in the second wavelength band.

The method may further include generating a consecutive plurality of data sets indicative of respective concentrations of the substance over time without removing the temperature probe from the volume or changing positions of the light source and the detector, each of the plurality of data sets including respective values corresponding to the internal temperature signal, the first and second initial power signal, and the first and second material absorption signal. The concentrations of the substance are continuously monitored by determining whether the concentrations or the consecutive plurality of data sets are within a tolerance. A warning output is generated when one or more of the concentrations or one or more of the consecutive plurality of data sets is outside the tolerance.

Measuring the internal temperature may include measuring to accuracy of 0.01 degree Kelvin or a lower temperature. The calculating may include determining the substance concentration based on a correlation of substance concentration with the values corresponding to the internal temperature signal, the first and second initial power signal, and the first and second material absorption signal.

The additional features that may be implemented in the present method may also be implemented in other methods and apparatuses herein.

According to one apparatus, a substance concentration monitoring apparatus includes a casing, a slot in the casing sized and positioned to receive an ear lobe, and a temperature probe inside the casing sized and positioned to extend into the slot and to be received into a healed piercing of the ear lobe when the ear lobe is placed in the slot. The temperature probe includes a thermally conductive needle with a thermistor inside the needle or with a resistance temperature detector.

A light source is inside the casing and is configured to produce a first near infrared (NIR) beam in a first wavelength band and to produce a second NIR beam in a second wavelength band. The light source is positioned and oriented to direct the first and second NIR beams through the ear lobe when the ear lobe is placed in the slot. The first wavelength band includes a wavelength at which an absorption peak exists in a NIR absorption spectrum of the substance. The substance exhibits no absorption or negligible absorption in the second wavelength band.

A NIR detector is inside the casing on an opposing side of the slot from the light source and is positioned to be on an opposing side of the ear lobe from the light source when the ear lobe is placed in the slot. The detector is aligned with the light source to receive the first and second NIR beams from the light source directed through and exiting from the ear lobe when the temperature probe is inserted into the piercing. The NIR detector is configured to detect an exit power of the first NIR beam and the second NIR beam.

The temperature probe is positioned in proximity to the light source and the detector such that a temperature of the ear lobe measured by the temperature probe corresponds to an internal temperature of a volume of the ear lobe through which the first and second NIR beams are directed when the temperature probe is inserted into the piercing.

Additional features may be implemented in the present apparatus. By way of example, the substance may be glucose. The light source may be a single NIR emitter configured to generate selectively a NIR beam in the first wavelength band and to generate selectively a NIR beam in the second wavelength band. Correspondingly, the detector may be a single detector configured to detect NIR beams both in the first wavelength band and in the second wavelength band. The detector may include an interference filter configured to pass light within the first wavelength band and block light within the second wavelength band.

Alternatively, the light source may be a first NIR emitter configured to generate a first NIR beam in the first wavelength band and a different second NIR emitter configured to generate a second NIR beam in the second wavelength band. Correspondingly, the detector may be a first detector configured to detect a NIR beam in the first wavelength band and aligned with the first NIR emitter and a different second detector configured to detect a NIR beam in the second wavelength band and aligned with the second NIR emitter. The first detector may include a first filter having an interference filter configured to pass light within the first wavelength band and block light within the second wavelength band. The second detector may include a second filter with an interference filter configured to block light within the first wavelength band and pass light within the second wavelength band. The light source may include a power detector configured to detect an initial power of the first NIR beam and the second NIR beam.

The apparatus may further include a processor and a non-transitory computer-readable medium storing instructions that, when executed by the processor, causes the processor to initiate or perform operations. One operation includes generating a consecutive plurality of data sets indicative of respective concentrations of the substance over time without removing the temperature probe from the volume or changing positions of the light source and the detector, each of the plurality of data sets including respective values corresponding to the internal temperature, the initial power of the first and second NIR beams, and the exit power of the first and second NIR beams. Another operation includes continuously monitoring the concentrations of the substance by determining whether the concentrations or the consecutive plurality of data sets are within a tolerance. A further operation includes generating a warning output when one or more of the concentrations or one or more of the consecutive plurality of data sets is outside the tolerance. The temperature probe may exhibit a measurement accuracy of 0.01 degree Kelvin or a lower temperature.

The additional features that may be implemented in the present apparatus may also be implemented in other apparatuses and methods herein.

The inventors expressly contemplate that the various options described herein for individual methods and apparatuses are not intended to be so limited except where incompatible. The features and benefits of individual methods herein may also be used in combination with apparatuses and other methods described herein even though not specifically indicated elsewhere. Similarly, the features and benefits of individual apparatuses herein may also be used in combination with methods and other apparatuses described herein even though not specifically indicated elsewhere.

In compliance with the statute, the embodiments have been described in language more or less specific as to structural and methodical features. It is to be understood, however, that the embodiments are not limited to the specific features shown and described. The embodiments are, therefore, claimed in any of their forms or modifications within the proper scope of the appended claims appropriately interpreted in accordance with the doctrine of equivalents.

TABLE OF REFERENCE NUMERALS FOR FIGURES 1 needle
2 thermistor
3 earlobe
4 light source
5 light source
6 detector assembly
7 detector assembly
8 casing
9 tube
10 light chassis
11 detector chassis
12 control box
13 needle tip
14 thermal isolation
15 thermal isolation
16 optical path
17 optical path
18 earring assembly
20 measurement system
22 communication
24 communication

What is claimed is:

1. A substance concentration monitoring method comprising:
    inserting a temperature probe noninvasively into a volume of a body in which a concentration of a substance is to be measured, the temperature probe contacting an internal surface of the volume;
    measuring an internal temperature of the volume as determined by heat transfer from the internal surface to the inserted temperature probe and producing an internal temperature signal indicative of the internal temperature;
    while the volume exhibits the internal temperature, directing an incident first near infrared (NIR) beam in a first wavelength band from a light source into a portion of the volume, the first wavelength band including a wavelength at which an absorption peak exists in a NIR absorption spectrum of the substance;
    while directing the incident first NIR beam, detecting an initial power of the incident first NIR beam and producing a first initial power signal indicative of the first initial power;
    while the volume exhibits the internal temperature, receiving the first NIR beam exiting from the portion of the volume onto a detector;
    while receiving the exiting first NIR beam, detecting an exit power of the exiting first NIR beam not absorbed in the volume and producing a first material absorption signal indicative of the first exit power;

while the volume exhibits the internal temperature, directing an incident second NIR beam in a second wavelength band from the light source into the portion of the volume, the substance exhibiting no absorption or negligible absorption in the second wavelength band;

while directing the incident second NIR beam, detecting an initial power of the incident second NIR beam and producing a second initial power signal indicative of the second initial power;

while the volume exhibits the internal temperature, receiving a second NIR beam exiting from the portion of the volume onto the detector;

while receiving the exiting second NIR beam, detecting an exit power of the exiting second NIR beam not absorbed in the volume and producing a second material absorption signal indicative of the second exit power; and calculating substance concentration in the portion of the volume based on values corresponding to the internal temperature signal, the first and second initial power signal, and the first and second material absorption signal.

2. The method of claim 1 wherein the substance is glucose.

3. The method of claim 1 wherein inserting the temperature probe noninvasively comprises inserting the temperature probe into a healed piercing of an ear lobe and the light source and the detector are positioned on opposing sides of the ear lobe.

4. The method of claim 1 wherein:
the light source comprises a single NIR emitter configured to generate selectively a NIR beam in the first wavelength band and to generate selectively a NIR beam in the second wavelength band; and
the detector comprises a single detector configured to detect the NIR beams both in the first wavelength band and in the second wavelength band.

5. The method of claim 1 wherein:
the light source comprises a first NIR emitter configured to generate a first NIR beam in the first wavelength band and a different second NIR emitter configured to generate a second NIR beam in the second wavelength band; and
the detector comprises a first detector configured to detect the NIR beam in the first wavelength band and a different second detector configured to detect the NIR beam in the second wavelength band.

6. The method of claim 1 further comprising:
generating a consecutive plurality of data sets indicative of respective concentrations of the substance over time without removing the temperature probe from the volume or changing positions of the light source and the detector, each of the plurality of data sets including respective values corresponding to the internal temperature signal, the first and second initial power signal, and the first and second material absorption signal;
continuously monitoring the concentrations of the substance by determining whether the concentrations or the consecutive plurality of data sets are within a tolerance; and
generating a warning output when one or more of the concentrations or one or more of the consecutive plurality of data sets is outside the tolerance.

7. The method of claim 1 wherein measuring the internal temperature comprise measuring to accuracy of 0.01 degree Kelvin or a lower temperature.

8. The method of claim 1 wherein the calculating comprises determining the substance concentration based on a correlation of substance concentration with the values corresponding to the internal temperature signal, the first and second initial power signal, and the first and second material absorption signal.

9. The method of claim 1 wherein the first wavelength band is within the range of about 1130 nm to about 1190 nm or within the range of 1300 nm to 1500 nm and the second wavelength band is within the range of about 800 nm to about 905 nm or is within a range that includes 960 nm or 1120 nm.

10. A substance concentration monitoring apparatus comprising:
a casing;
a slot in the casing sized and positioned to receive an ear lobe;
a temperature probe inside the casing sized and positioned to extend into the slot and to be received into a healed piercing of the ear lobe when the ear lobe is placed in the slot, the temperature probe including a thermally conductive needle with a thermistor inside the needle or with a resistance temperature detector;
a light source inside the casing and configured to produce a first near infrared (NIR) beam in a first wavelength band and to produce a second NIR beam in a second wavelength band, the light source being positioned and oriented to direct the first and second NIR beams through the ear lobe when the ear lobe is placed in the slot;
the first wavelength band including a wavelength at which an absorption peak exists in a NIR absorption spectrum of the substance and the substance exhibiting no absorption or negligible absorption in the second wavelength band;
a NIR detector inside the casing on an opposing side of the slot from the light source and positioned to be on an opposing side of the ear lobe from the light source when the ear lobe is placed in the slot, the detector being aligned with the light source to receive the first and second NIR beams from the light source directed through and exiting from the ear lobe when the temperature probe is inserted into the piercing, the NIR detector being configured to detect an exit power of the first NIR beam and the second NIR beam;
the temperature probe being positioned in proximity to the light source and the detector such that a temperature of the ear lobe measured by the temperature probe corresponds to an internal temperature of a volume of the ear lobe through which the first and second NIR beams are directed when the temperature probe is inserted into the piercing.

11. The apparatus of claim 10 wherein the substance is glucose.

12. The apparatus of claim 10 wherein:
the light source comprises a single NIR emitter configured to generate selectively a NIR beam in the first wavelength band and to generate selectively a NIR beam in the second wavelength band; and
the detector comprises a single detector configured to detect NIR beams both in the first wavelength band and in the second wavelength band.

13. The apparatus of claim 10 wherein the detector comprises an interference filter configured to pass light within the first wavelength band and block light within the second wavelength band.

14. The apparatus of claim 10 wherein:
the light source comprises a first NIR emitter configured to generate a first NIR beam in the first wavelength band and a different second NIR emitter configured to generate a second NIR beam in the second wavelength band; and
the detector comprises a first detector configured to detect a NIR beam in the first wavelength band and aligned with the first NIR emitter and a different second detector configured to detect a NIR beam in the second wavelength band and aligned with the second NIR emitter.

15. The apparatus of claim 14 wherein the first detector comprises a first filter including an interference filter configured to pass light within the first wavelength band and block light within the second wavelength band and the second detector comprises a second filter including an interference filter configured to block light within the first wavelength band and pass light within the second wavelength band.

16. The apparatus of claim 10 wherein the light source comprises a power detector configured to detect an initial power of the first NIR beam and the second NIR beam.

17. The apparatus of claim 16 further comprising a processor and a non-transitory computer-readable medium storing instructions that, when executed by the processor, causes the processor to initiate or perform operations comprising:
generating a consecutive plurality of data sets indicative of respective concentrations of the substance over time without removing the temperature probe from the volume or changing positions of the light source and the detector, each of the plurality of data sets including respective values corresponding to the internal temperature, the initial power of the first and second NIR beams, and the exit power of the first and second NIR beams;
continuously monitoring the concentrations of the substance by determining whether the concentrations or the consecutive plurality of data sets are within a tolerance; and
generating a warning output when one or more of the concentrations or one or more of the consecutive plurality of data sets is outside the tolerance.

18. The apparatus of claim 10 wherein the temperature probe exhibits a measurement accuracy of 0.01 degree Kelvin or a lower temperature.

19. The apparatus of claim 10 wherein the first wavelength band is within the range of about 1130 nm to about 1190 nm or within the range of 1300 nm to 1500 nm and the second wavelength band is within the range of about 800 nm to about 905 nm or is within a range that includes 960 nm or 1120 nm.

* * * * *